(12) United States Patent
Chung et al.

(10) Patent No.: US 7,408,043 B2
(45) Date of Patent: Aug. 5, 2008

(54) NEUTRALIZING ANTIBODY AGAINST HGF

(75) Inventors: Junho Chung, Seoul (KR); Youngmi Hur, Seoul (KR)

(73) Assignee: National Cancer Center, Goyang-shi (KR)

( * ) Notice: Subject to any disclaimer, the term of this patent is extended or adjusted under 35 U.S.C. 154(b) by 0 days.

(21) Appl. No.: 10/578,836

(22) PCT Filed: Nov. 9, 2004

(86) PCT No.: PCT/KR2004/002888

§ 371 (c)(1),
(2), (4) Date: May 10, 2006

(87) PCT Pub. No.: WO2005/044848

PCT Pub. Date: May 19, 2005

(65) Prior Publication Data

US 2007/0036789 A1 Feb. 15, 2007

(30) Foreign Application Priority Data

Nov. 11, 2003 (KR) ...................... 10-2003-0079482

(51) Int. Cl.
*C07K 16/26* (2006.01)
(52) U.S. Cl. .................. 530/388.1; 530/388.22; 530/388.24; 530/387.1
(58) Field of Classification Search ........................ None
See application file for complete search history.

(56) References Cited

OTHER PUBLICATIONS

Cao,B et al. "Neutralizing monoclonal antibodies to hepatocyte growth factor/scatter factor (HGF/SF) display antiturmor activity in animal models" PNAS Jun. 2001, vol. 98(13):7443-8, See entire document.*
Lederman et al. Molecular Immunology 28: 1171-1181, 1991.*
Li et al. PNAS 77: 3211-3214, 1980.*
Bost et al. (Immunological Investigations, 1988, 17:577-586.*
Bendayan The Journal of Histochemistry and Cytochemistry, 1995, 43:881-886.*
Burr, A.W. et al., "Anti-hepatocyte Growth Factor Antibody Inhibits Hepatocyte Proliferation During Liver Regeneration," J. of Pathology, vol. 185: 298-302 (1998).
Di Nicola, M. et al. "Human bone marrow stromal cells suppress T-lymphocyte proliferation induced by cellular on nonspecific mitogenic stimula," Blood, vol. 99, No. 10, May 15, 2002, 3838-3843.
Tabor, K. et al., "Monoclonal Antibodies (MABS) to the NK1 Region of Human Hepatocyte Growth Factor (HGF) Block HGF Activity, " J. Cellular Biochemcistry, No. 18, part A, Jan. 16, 1994, p. 288.
Zaccolo M., et al., "Dimidiation of Fab fragments enables ready screening of phage antobodies that affect hepatocyte growth factor/scatter factor activity on target cells," Eur. J. Immunol., vol. 27, No. 3, 1997, 618-623.
Hu, C., et al., "Cloning and sequencing of variable region genes of Hab25 McAb agains hepatocellular carcinoma," Database Medline, XP-002447481, Database accession No. NLM10488420, June 1999.
Schmidt, N.O. et al., "Levels of Vascula Endothelial Growth Factor, Hepatocyte Growth Factor/Scatter Factor and Basic Fibroblast Growth Factor in Human Gliomas and Their Relation to Angiogenesis," Int. J. Cancer, 84, 10-18 (1999).
Lamszuz, K., et al., "Scatter Factor Promotes Motility of Human Glioma and Neuromicrovascular Endothelial Cells," Int. J. Cancer, 75, 19-28 (1998).

* cited by examiner

*Primary Examiner*—Phillip Gambel
*Assistant Examiner*—Sharon Wen
(74) *Attorney, Agent, or Firm*—Sughrue Mion, PLLC

(57) ABSTRACT

The neutralizing antibody against HGF binding to the inventive neutralizable epitope of HGF is capable of neutralizing HGF as a single agent, and can be effectively used for preventing and treating intractable diseases and cancers that are caused by binding of HGF to its receptor Met.

6 Claims, 8 Drawing Sheets

SEQUENCE LISTING

<160> NUMBER OF SEQ ID NOS: 35

<210> SEQ ID NO 1
<211> LENGTH: 38
<212> TYPE: DNA
<213> ORGANISM: Artificial Sequence
<220> FEATURE:
<223> OTHER INFORMATION: Vkappa 5' sense primer RSCVK1

<400> SEQUENCE: 1
gggcccaggc ggccgagctc gtgmtgaccc agactcca                    38

<210> SEQ ID NO 2
<211> LENGTH: 38
<212> TYPE: DNA
<213> ORGANISM: Artificial Sequence
<220> FEATURE:
<223> OTHER INFORMATION: Vkappa 5' sense primer RSCVK2

<400> SEQUENCE: 2
gggcccaggc ggccgagctc gatmtgaccc agactcca                    38

<210> SEQ ID NO 3
<211> LENGTH: 38
<212> TYPE: DNA
<213> ORGANISM: Artificial Sequence
<220> FEATURE:
<223> OTHER INFORMATION: Vkappa 5' sense primer RSCVK3

<400> SEQUENCE: 3
gggcccaggc ggccgagctc gtgatgaccc agactgaa                    38

<210> SEQ ID NO 4
<211> LENGTH: 42
<212> TYPE: DNA
<213> ORGANISM: Artificial Sequence
<220> FEATURE:
<223> OTHER INFORMATION: Vkappa 3' reverse primer RHybK1-B

<400> SEQUENCE: 4
agatggtgca gccacagttc gtttgatttc cacattggtg cc               42

<210> SEQ ID NO 5
<211> LENGTH: 42
<212> TYPE: DNA
<213> ORGANISM: Artificial Sequence
<220> FEATURE:
<223> OTHER INFORMATION: Vkappa 3' reverse primer RHybK2-B

<400> SEQUENCE: 5
agatggtgca gccacagttc gtaggatctc cagctcggtc cc               42

<210> SEQ ID NO 6
<211> LENGTH: 42
<212> TYPE: DNA
<213> ORGANISM: Artificial Sequence
<220> FEATURE:
<223> OTHER INFORMATION: Vkappa 3' reverse primer RHybK3-B

<400> SEQUENCE: 6
agatggtgca gccacagttc gtttgacsac cacctcggtc cc               42

<210> SEQ ID NO 7
<211> LENGTH: 40

```
<210> SEQ ID NO 7
<211> LENGTH: 40
<212> TYPE: DNA
<213> ORGANISM: Artificial Sequence
<220> FEATURE:
<223> OTHER INFORMATION: Vlambda 5' sense primer RSClambda1

<400> SEQUENCE: 7
gggcccaggc ggccgagctc gtgctgactc agtcgccctc                             40

<210> SEQ ID NO 8
<211> LENGTH: 45
<212> TYPE: DNA
<213> ORGANISM: Artificial Sequence
<220> FEATURE:
<223> OTHER INFORMATION: Vlambda 3' reverse primer RHybL-B

<400> SEQUENCE: 8
agatggtgca gccacagttc ggcctgtgac ggtcagctgg gtccc                       45

<210> SEQ ID NO 9
<211> LENGTH: 42
<212> TYPE: DNA
<213> ORGANISM: Artificial Sequence
<220> FEATURE:
<223> OTHER INFORMATION: VH 5' sense primer RHyVH1

<400> SEQUENCE: 9
gctgcccaac cagccatggc ccagtcggtg gaggagtccr gg                          42

<210> SEQ ID NO 10
<211> LENGTH: 42
<212> TYPE: DNA
<213> ORGANISM: Artificial Sequence
<220> FEATURE:
<223> OTHER INFORMATION: VH 5' sense primer RHyVH2

<400> SEQUENCE: 10
gctgcccaac cagccatggc ccagtcggtg aaggagtccg ag                          42

<210> SEQ ID NO 11
<211> LENGTH: 42
<212> TYPE: DNA
<213> ORGANISM: Artificial Sequence
<220> FEATURE:
<223> OTHER INFORMATION: VH 5' sense primer RHyVH3

<400> SEQUENCE: 11
gctgcccaac cagccatggc ccagtcgytg gaggagtccg gg                          42

<210> SEQ ID NO 12
<211> LENGTH: 44
<212> TYPE: DNA
<213> ORGANISM: Artificial Sequence
<220> FEATURE:
<223> OTHER INFORMATION: VH 5' sense primer RHyVH4

<400> SEQUENCE: 12
gctgcccaac cagccatggc ccagsagcag ctgrtggagt ccgg                        44

<210> SEQ ID NO 13
<211> LENGTH: 45
<212> TYPE: DNA
<213> ORGANISM: Artificial Sequence
<220> FEATURE:
<223> OTHER INFORMATION: VH 3' reverse primer RHyIgGCH1-B

<400> SEQUENCE: 13
```

```
cgatgggccc ttggtggagg ctgargagay ggtgaccagg gtgcc                    45
```

<210> SEQ ID NO 14
<211> LENGTH: 24
<212> TYPE: DNA
<213> ORGANISM: Artificial Sequence
<220> FEATURE:
<223> OTHER INFORMATION: Sense primer HKC-F for amplification of the
      human Ckappa region and the pelB leader sequence from a cloned
      human Fab

<400> SEQUENCE: 14

```
cgaactgtgg ctgcaccatc tgtc                                           24
```

<210> SEQ ID NO 15
<211> LENGTH: 21
<212> TYPE: DNA
<213> ORGANISM: Artificial Sequence
<220> FEATURE:
<223> OTHER INFORMATION: Reverse primer Lead-B for amplification of the
      human Ckappa region and the pelB leader sequence from a cloned
      human Fab

<400> SEQUENCE: 15

```
ggccatggct ggttgggcag c                                              21
```

<210> SEQ ID NO 16
<211> LENGTH: 24
<212> TYPE: DNA
<213> ORGANISM: Artificial Sequence
<220> FEATURE:
<223> OTHER INFORMATION: Sense primer HIgGCH1-F for amplification of the
      human CH1 Chain from a cloned human Fab

<400> SEQUENCE: 16

```
gcctccacca agggcccatc ggtc                                           24
```

<210> SEQ ID NO 17
<211> LENGTH: 21
<212> TYPE: DNA
<213> ORGANISM: Artificial Sequence
<220> FEATURE:
<223> OTHER INFORMATION: Reverse primer dpseq for amplification of the
      human CH1 Chain from a cloned human Fab

<400> SEQUENCE: 17

```
agaagcgtag tccggaacgt c                                              21
```

<210> SEQ ID NO 18
<211> LENGTH: 41
<212> TYPE: DNA
<213> ORGANISM: Artificial Sequence
<220> FEATURE:
<223> OTHER INFORMATION: Sense primer RSC-F for PCR assembly of rabbit
      VL sequences with the human Ckappa PCR Product

<400> SEQUENCE: 18

```
gaggaggagg aggaggaggc ggggcccagg cggccgagct c                        41
```

<210> SEQ ID NO 19
<211> LENGTH: 21
<212> TYPE: DNA
<213> ORGANISM: Artificial Sequence
<220> FEATURE:
<223> OTHER INFORMATION: Sense primer LeadVH for PCR assembly of rabbit
      VH sequences with the human CH1 PCR product

<400> SEQUENCE: 19
gctgcccaac cagccatggc c                                              21

<210> SEQ ID NO 20
<211> LENGTH: 39
<212> TYPE: DNA
<213> ORGANISM: Artificial Sequence
<220> FEATURE:
<223> OTHER INFORMATION: Reverse primer dp-EX for PCR assembly of
      chimeric light-chain sequences with chimeric heavy-chain (Fd)
      sequences

<400> SEQUENCE: 20
gaggaggagg aggaggagag aagcgtagtc cggaacgtc                            39

<210> SEQ ID NO 21
<211> LENGTH: 20
<212> TYPE: DNA
<213> ORGANISM: Artificial Sequence
<220> FEATURE:
<223> OTHER INFORMATION: sequencing primer

<400> SEQUENCE: 21
agaaacacaa agtctacgcc                                                 20

<210> SEQ ID NO 22
<211> LENGTH: 20
<212> TYPE: DNA
<213> ORGANISM: Artificial Sequence
<220> FEATURE:
<223> OTHER INFORMATION: sequencing primer

<400> SEQUENCE: 22
gttgggcagc gagtaataac                                                 20

<210> SEQ ID NO 23
<211> LENGTH: 348
<212> TYPE: DNA
<213> ORGANISM: Artificial Sequence
<220> FEATURE:
<223> OTHER INFORMATION: nucleotide sequence encoding VH region of
      clone 61

<400> SEQUENCE: 23
caggagcagc tgatggagtc cggggggtcgc ctggtcaatc ctggcgaatc cctgacactc      60
acctgcaaag cctctggatt caccttcagt agctactaca tgagctgggt ccgccaggct     120
ccagggaagg ggctggagtg gatcggatac attggtacta gtagtggtac cacttactac     180
gcgaactctg tgaagggccg attcaccatc tccagcgaca acgcccagaa taccgtattt     240
ctgcgaatga ccagtctcac agactcggac acggccacct atttctgtgc aagagggctg     300
ggcagaatca acttgtgggg cccaggcacc ctggtcaccg tctcttca                 348

<210> SEQ ID NO 24
<211> LENGTH: 327
<212> TYPE: DNA
<213> ORGANISM: Artificial Sequence
<220> FEATURE:
<223> OTHER INFORMATION: nucleotide sequence encoding VL region of
      clone 61

<400> SEQUENCE: 24
gagctcgtgc tgacccagac tccatcctct atgtctgcag ctgtgggagg cacagtcacc      60
atcaattgcc aggccagtca gagtgttagc aactacttag cctggtatca gcagaaacca     120

```
gggcagcctc ccaagctcct gatctacagg gcatccactc tggcatctgg ggtcccatcg    180
cgtttcagcg gcagtggatc tgggacagag ttcactctca ccatcagtgg catgaaggct    240
gaagatgctg ccacttatta ctgtcaaagt ggttattata gtgctggtgc gacttttgga    300
ggtggcacca atgtggaaat caaacga                                         327
```

<210> SEQ ID NO 25
<211> LENGTH: 348
<212> TYPE: DNA
<213> ORGANISM: Artificial Sequence
<220> FEATURE:
<223> OTHER INFORMATION: nucleotide sequence encoding VH region of clone 68

<400> SEQUENCE: 25

```
cagcagcagc tggtggagtc cggggtcgc ctggtcaatc ctggcgaatc cctgacactc     60
acctgcaaag cctctggatt caccttcagt acctactaca tgagctgggt ccgccaggct    120
ccagggaagg ggctagagtg gatcggatac attggtacta gtagtggtac cacttactac    180
gcgaactctg tgaagggccg attcaccatc tccagcgaca cgcccagaa taccgtattt     240 ctgcaaatga ccagtctgac agactcggac acggccacct atttctgtgc aagagggctg    300
ggcagaatta acttgtgggg cccaggcacc ctggtcaccg tctcctca                 348
```

<210> SEQ ID NO 26
<211> LENGTH: 327
<212> TYPE: DNA
<213> ORGANISM: Artificial Sequence
<220> FEATURE:
<223> OTHER INFORMATION: nucleotide sequence encoding VL region of clone 68

<400> SEQUENCE: 26

```
gagctcgatc tgacccagac tccatcctct gtgtctgcag ctgtgggagg cacagtcacc     60
atcaattgcc aggccagtca gagtgttagc aacctcttag cctggtatca gcagaaacca    120
gggcagcctc ccaagctcct gatttatggt gcatccaatc tggaatctgg ggtcccatcg    180
cgtttccgtg gcagtggatc tgggacagag ttcactctca ccatcagtgg catgaaggct    240
gaagatgctg ccacttatta ctgtcaaagt ggttattata gtgctggtgc gacttttgga    300
gctggcacca atgtggaaat caaacga                                         327
```

<210> SEQ ID NO 27
<211> LENGTH: 116
<212> TYPE: PRT
<213> ORGANISM: Artificial Sequence
<220> FEATURE:
<223> OTHER INFORMATION: amino acid sequence of VH region of clone 61

<400> SEQUENCE: 27

Gln Glu Gln Leu Met Glu Ser Gly Gly Arg Leu Val Asn Pro Gly Glu
 1               5                  10                  15

Ser Leu Thr Leu Thr Cys Lys Ala Ser Gly Phe Thr Phe Ser Ser Tyr
            20                  25                  30

Tyr Met Ser Trp Val Arg Gln Ala Pro Gly Lys Gly Leu Glu Trp Ile
        35                  40                  45

Gly Tyr Ile Gly Thr Ser Ser Gly Thr Thr Tyr Tyr Ala Asn Ser Val
    50                  55                  60

Lys Gly Arg Phe Thr Ile Ser Ser Asp Asn Ala Gln Asn Thr Val Phe
65                  70                  75                  80

```
Leu Arg Met Thr Ser Leu Thr Asp Ser Asp Thr Ala Thr Tyr Phe Cys
                 85                  90                  95

Ala Arg Gly Leu Gly Arg Ile Asn Leu Trp Gly Pro Gly Thr Leu Val
            100                 105                 110

Thr Val Ser Ser
        115

<210> SEQ ID NO 28
<211> LENGTH: 109
<212> TYPE: PRT
<213> ORGANISM: Artificial Sequence
<220> FEATURE:
<223> OTHER INFORMATION: amino acid sequence of VL region of clone 61

<400> SEQUENCE: 28

Glu Leu Val Leu Thr Gln Thr Pro Ser Ser Met Ser Ala Ala Val Gly
 1               5                  10                  15

Gly Thr Val Thr Ile Asn Cys Gln Ala Ser Gln Ser Val Ser Asn Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Gly Tyr Tyr Ser Ala Gly
                85                  90                  95

Ala Thr Phe Gly Gly Gly Thr Asn Val Glu Ile Lys Arg
            100                 105

<210> SEQ ID NO 29
<211> LENGTH: 116
<212> TYPE: PRT
<213> ORGANISM: Artificial Sequence
<220> FEATURE:
<223> OTHER INFORMATION: amino acid sequence of VH region of clone 68

<400> SEQUENCE: 29

Gln Gln Gln Leu Val Glu Ser Gly Gly Arg Leu Val Asn Pro Gly Glu
 1               5                  10                  15

Ser Leu Thr Leu Thr Cys Lys Ala Ser Gly Phe Thr Phe Ser Thr Tyr
            20                  25                  30

Tyr Met Ser Trp Val Arg Gln Ala Pro Gly Lys Gly Leu Glu Trp Ile
        35                  40                  45

Gly Tyr Ile Gly Thr Ser Ser Gly Thr Thr Tyr Tyr Ala Asn Ser Val
    50                  55                  60

Lys Gly Arg Phe Thr Ile Ser Ser Asp Asn Ala Gln Asn Thr Val Phe
65                  70                  75                  80

Leu Gln Met Thr Ser Leu Thr Asp Ser Asp Thr Ala Thr Tyr Phe Cys
                85                  90                  95

Ala Arg Gly Leu Gly Arg Ile Asn Leu Trp Gly Pro Gly Thr Leu Val
            100                 105                 110

Thr Val Ser Ser
        115

<210> SEQ ID NO 30
<211> LENGTH: 109
<212> TYPE: PRT
<213> ORGANISM: Artificial Sequence
```

<220> FEATURE:
<223> OTHER INFORMATION: amino acid sequence of VL region of clone 68

<400> SEQUENCE: 30

Glu Leu Asp Leu Thr Gln Thr Pro Ser Ser Val Ser Ala Ala Val Gly
1               5                   10                  15

Gly Thr Val Thr Ile Asn Cys Gln Ala Ser Gln Ser Val Ser Asn Leu
            20                  25                  30

Leu Ala Trp Tyr Gln Gln Lys Pro Gly Gln Pro Pro Lys Leu Leu Ile
        35                  40                  45

Tyr Gly Ala Ser Asn Leu Glu Ser Gly Val Pro Ser Arg Phe Arg Gly
    50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Gly Tyr Tyr Ser Ala Gly
                85                  90                  95

Ala Thr Phe Gly Ala Gly Thr Asn Val Glu Ile Lys Arg
            100                 105

<210> SEQ ID NO 31
<211> LENGTH: 20
<212> TYPE: DNA
<213> ORGANISM: Artificial Sequence
<220> FEATURE:
<223> OTHER INFORMATION: sequencing primer

<400> SEQUENCE: 31
ccctcatagt tagcgtaacg                                         20

<210> SEQ ID NO 32
<211> LENGTH: 12
<212> TYPE: PRT
<213> ORGANISM: Artificial Sequence
<220> FEATURE:
<223> OTHER INFORMATION: neutralizable epitope of HGF

<400> SEQUENCE: 32

His His Pro His Phe Lys Pro Val Ser Asn Ser Arg
1               5                   10

<210> SEQ ID NO 33
<211> LENGTH: 12
<212> TYPE: PRT
<213> ORGANISM: Artificial Sequence
<220> FEATURE:
<223> OTHER INFORMATION: neutralizable epitope of HGF

<400> SEQUENCE: 33

Lys Ser Leu Ser Arg His Asp His Ile His His His
1               5                   10

<210> SEQ ID NO 34
<211> LENGTH: 36
<212> TYPE: DNA
<213> ORGANISM: Artificial Sequence
<220> FEATURE:
<223> OTHER INFORMATION: nucleotide sequence encoding SEQ. ID. No. 32

<400> SEQUENCE: 34
catcatccgc attttaagcc tgtgtctaat agtcgt                       36

<210> SEQ ID NO 35
<211> LENGTH: 36

```
-continued

<212> TYPE: DNA
<213> ORGANISM: Artificial Sequence
<220> FEATURE:
<223> OTHER INFORMATION: nucleotide sequence encoding SEQ. ID. No. 33

<400> SEQUENCE: 35
aagtctctta gtcggcatga tcatattcat catcat                                    36
```

NEUTRALIZING ANTIBODY AGAINST HGF

This is a National Stage Application under 35 U.S.C. 371 of PCT/KR2004/002888 filed Nov. 9, 2004, which claims priority from Korean Patent Application 10-2003-0079482 filed Nov. 11, 2003, all of which are incorporated herein by reference.

FIELD OF THE INVENTION

The present invention relates to a neutralizable epitope of HGF (hepatocyte growth factor) inhibiting the binding of HGF to a receptor thereof and a neutralizing antibody against HGF which is capable of neutralizing HGF as a single agent by binding to said neutralizable epitope of HGF.

BACKGROUND OF THE INVENTION

HGF (hepatocyte growth factor) is a multifunctional heterodimeric polypeptide produced by mesenchymal cells. HGF is composed of an alpha-chain containing an N-terminal domain and four kringle domains (NK4) covalently linked to a serine protease-like beta-chain C-terminal domain (see FIG. 1). Human HGF is synthesized as a biologically inactive single chain precursor consisting of 728 amino acids with a 29 amino acid signal peptide which is not present in the mature protein. Biologically active HGF is achieved through cleavage at the R494 residue by a specific, extracellular serum serine protease. The active HGF thus achieved is a fully active heterodimer which is composed of disulfide linked 69 kDa alpha-chain and 34 kDa beta-chain. However, the overall tertiary structure of HGF is still unknown and it has not yet been clarified which of these domains is responsible for the specific functions of HGF (Maulik et al., *Cytokine & Growth Factor Reviews* 13(1): 1-59, 2002).

The binding of HGF to its receptor, Met, induces the growth and scattering of various cell types, mediates the epithelial mesenchymal transitions and the formation of tubules and lumens, and promotes angiogenesis. Both Met and HGF knockout mice are embryonic lethal and show developmental defects in placenta, fetal liver and limb/muscle formation (Cao et al., *PNAS* 98(13): 7443-7448, 2001; Gmyrek et al., *American Journal of Pathology* 159(2): 579-590, 2001).

Met was originally isolated as a product of a human oncogene, trp-met, which encodes a constitutively active altered protein kinase with transforming activity. Met activation has also been shown to remarkably enhance the metastastic spread of cancer stemming from its stimulatory influence of processes such as angiogenesis, cell motility, and cell surface protease regulation (Wielenga et al., *American Journal of Pathology* 157(5): 1563-1573, 2000). Since Met was reported to be over-expressed in various human cancers of liver, prostate, colon, breast, brain and skin (Maulik et al, supra), it has been regarded as an important target factor for the prevention and treatment of cancer. Further, it has been reported that malaria infection depends on activation of the HGF receptor by secreted HGF, and accordingly, HGF and its receptor are identified as potential targets for new approaches to malaria prevention (Carrolo M, et al., *Nat. Med.* 9(11): 1363-1369, 2003). It has been also discovered the possibility that HGF may be found in association with the pathologic changes which occur in Alzheimer's disease (Fenton H, et al., *Brain Res.* 779(1-2): 262-270, 1998). Furthermore, it has been found that HGF is definitely involved in enhancing cutaneous wound healing processes, including re-epithelialization, neovascularization and granulation tissue formation (Yoshida S, et al., *J. Invest. Dermatol.* 120(2): 335-343, 2003).

Meanwhile, selective neutralization of tumor-associated growth factors or cytokines and their receptors, which play crucial roles in the development and spread of cancer, has always been an attractive strategy for the development of anti-cancer drugs. Recently, numerous therapeutic monoclonal antibodies (mAbs) for these targets, e.g., herceptin, and anti-angiopoietin human mAbs have been developed using recombinant antibody technologies such as phage display of combinational antibody library.

It is well known that polyclonal antibodies against HGF block many of HGF biological functions. In addition, it has been recently reported that mixtures of neutralizing mAbs against HGF display anti-tumor activity in animal models (Cao et al., *PNAS* 198(13): 7443-7448, 2001). In particular, Cao et al. disclosed that three or more of the epitopes, possibly two for the Met receptor and one for heparin, need to be blocked in order to inhibit HGF activity in vivo and in vitro, and a mixture of at least 3 mAbs is capable of neutralizing HGF in an in vitro experiment.

However, there has been reported no monoclonal antibody that can neutralize HGF as a single agent and inhibit cell scattering activity in vitro.

SUMMARY OF THE INVENTION

Accordingly, it is an object of the present invention to provide a neutralizable epitope of HGF which inhibits the binding of HGF to a receptor thereof.

Other objects of the present invention are to provide:

a polynucleotide encoding said neutralizable epitope;

a neutralizing antibody against HGF which is capable of neutralizing HGF as a single agent by binding to said neutralizable epitope;

use of said neutralizing antibody for preventing and treating intractable diseases and cancers;

a pharmaceutical composition comprising said neutralizing antibody and a pharmaceutically acceptable carrier for preventing and treating intractable diseases and cancers; and a method for preventing and treating intractable diseases and cancers, which comprises administering said neutralizing antibody to a patient.

In accordance with one aspect of the present invention, there is provided a neutralizable epitope of HGF having the amino acid sequence of SEQ ID NO: 32 or 33.

In accordance with another aspect of the present invention, there is provided a neutralizing antibody against HGF binding to said neutralizable epitope which comprises $V_H$ region having the amino acid sequence of SEQ ID NO: 27 or 29 and $V_L$ region having the amino acid sequence of SEQ ID NO: 28 or 30.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

Figure 1:
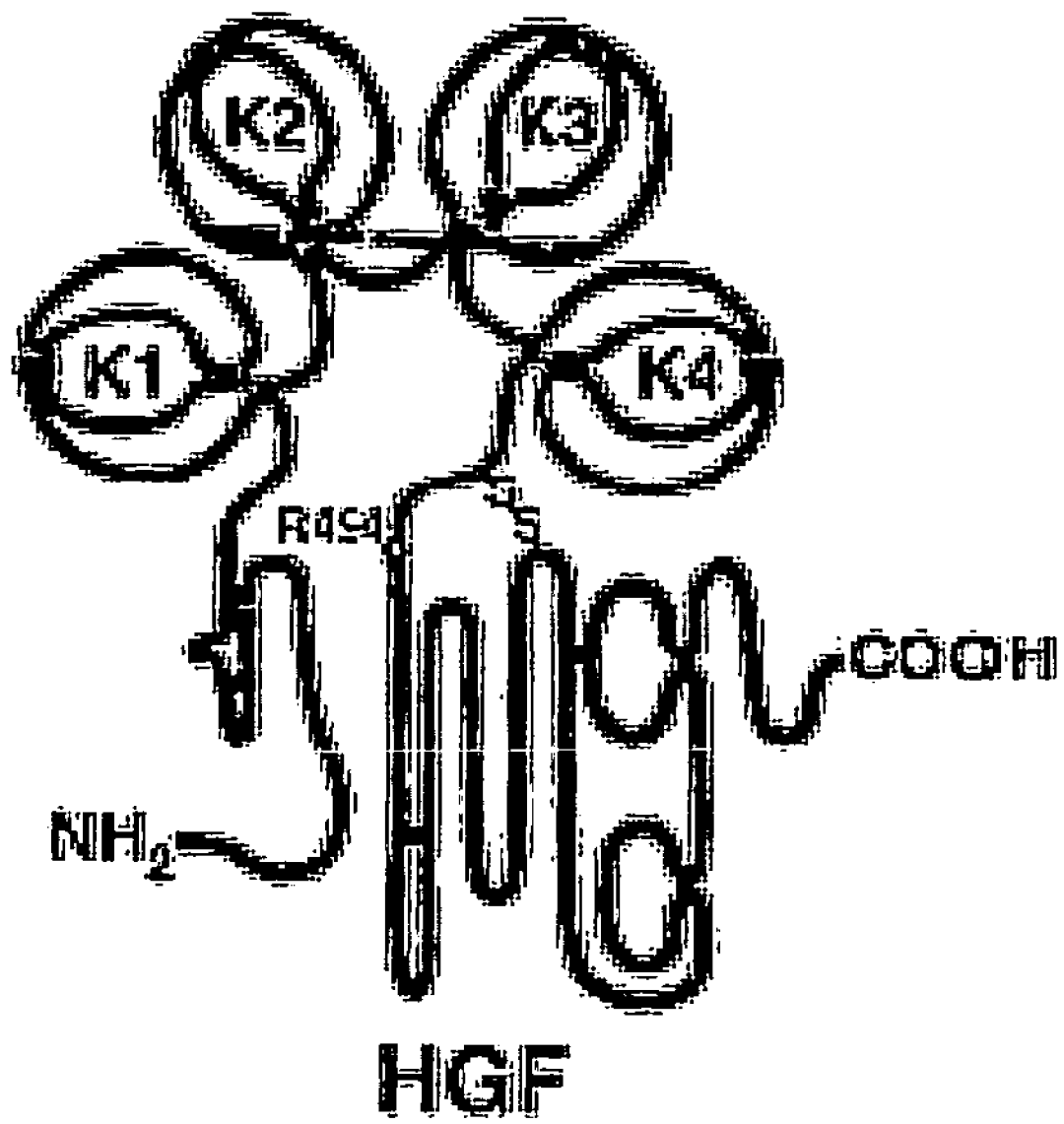
FIG. 1: the structure of HGF.

As used herein, the term "neutralizable epitope" includes any protein determinant which is capable of inhibiting the binding of HGF to its receptor, c-Met. Epitopic determinants usually consist of chemically active surface groupings of molecules such as amino acids or sugar side chains and usually have specific tertiary structural features, as well as specific charge characteristics. Preferably, the inventive neutralizable epitope is a polypeptide comprising the amino acid sequence of SEQ ID NO: 32 or 33.

The term "neutralizing antibody" refers to an antibody which is capable of specifically binding to the neutralizable epitope of HGF and substantially inhibiting or eliminating the biologically activity of HGF. Typically, a neutralizing antibody will inhibit such biologically activity of HGF at least by about 50%, and preferably by greater than 80%. The neutralizing antibody of the invention is especially useful in therapeutic applications: to prevent or treat intractable diseases and cancers.

The present invention provides a polypeptide having the amino acid sequence of SEQ ID NO: 32 or 33 which functions as a neutralizable epitope of HGF.

In order to prepare the neutralizable epitope of HGF in accordance with the present invention, an ELISA study is conducted to examine whether antisera from the immunized animals with HGF bind to a recombinant human HGF; and the study has shown that antisera from the HGF immunized animals specifically bind to HGF. Then, total RNA is extracted from the HGF immunized animals and subjected to cDNA synthesis.

To amplify the variable region comprising rabbit light chain ($V_L$) ($V_\kappa$, $V_\lambda$) and heavy chain ($V_H$) and the constant region comprising human $C_\kappa$ and $C_{H1}$, PCRs are performed by using the synthesized cDNA as a template and primer combinations of SEQ ID NOs: 1 to 20, and then, light and heavy chains of rabbit/human chimeric antibody are amplified by using the PCR products obtained above as templates. After the amplified rabbit $V_L$ and $V_H$ sequences are combined with the amplified human $C_\kappa$ and $C_{H1}$ sequences, final PCR products encoding a library of antibody fragments (Fab) are cloned into an expression vector, and the resulting vector is transformed into a host cell, e.g., *E. coli*, to construct a chimeric rabbit/human Fab library. The vector and host cell employable in the present invention include all expression vectors and *E. coli* strains conventionally used in the art without limit, but it is preferable to use phagemid vector pComb3X (the Scripps Research Institute, CA, USA) as an expression vector and *E. Coli* ER2537 (NEB) as a host cell.

Phage clones containing anti-HGF Fab are selected by EIA using HGF-coated ELISA plates and anti-human goat Fab polyclonal antibodies. Phage clones selected above are designated H61 (clone 61) and H68 (clone 68).

H61 and H68 clones are subjected to nucleotide sequencing and their amino acid sequences are determined from the analyzed nucleotide sequences, respectively. In a preferred embodiment of the present invention, nucleotide sequencing is performed according to the dye-labeled primer sequencing method (Chung et al., *J. Cancer Res. Clin. Oncol.* 128: 641-649, 2002). As a result, it has been found that H61 clone is composed of $V_H$ and $V_L$ regions having the nucleotide sequences of SEQ ID NOs: 23 and 24, respectively; and H68 clone comprises $V_H$ and $V_L$ regions having the nucleotide sequences of SEQ ID NOs: 25 and 26, respectively.

The amino acid sequences of the respective $V_H$ and $V_L$ regions of H61 and H68 clones from the analyzed nucleotide sequences suggest that H61 clone is composed of $V_H$ region having the amino acid sequence of SEQ ID NO: 28 and $V_L$ region having the amino acid sequence of SEQ ID NO: 28; and H68 clone, $V_H$ region having the amino acid sequence of SEQ ID NO: 29 and $V_L$ region having the amino acid sequence of SEQ ID NO: 30.

Analysis of the framework region (FR) and complementarity determining region (CDR) in the amino acid sequences of H61 and H68 clones has shown that each of $V_H$ and $V_L$ regions of H61 and H68 clones has 4 FRs and 3 CDRs (see Table 2).

To define a neutralizable epitope of HGF, H61 and H68 clones are enriched through the panning by using phage display of combinatorial peptide library, and the phage pools so amplified are subjected to EIA using anti-HGF H61 Fab or anti-HGF H68 Fab and anti-HGF H61 Fab- or anti-HGF H68 Fab-coated ELISA plates. Phage clones showing the binding affinity to anti-HGF H61 and H68 Fabs are thus selected. In a preferred embodiment of the present invention, the PHD peptide library (New England Biolob) is employed as a peptide library.

Figure 6:
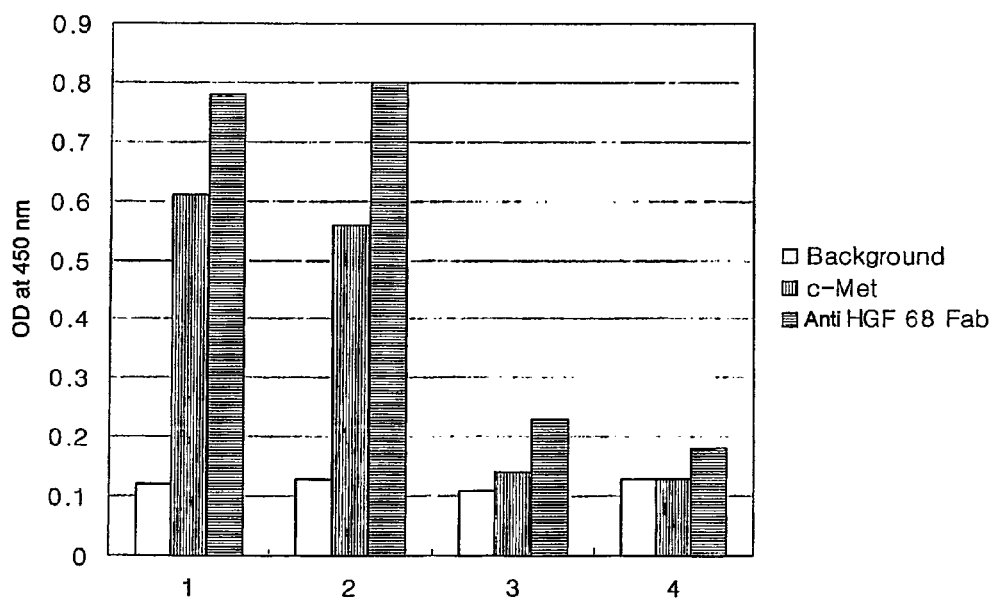
FIG. 6: the binding level of a phage containing the inventive neutralizable epitope to c-MET,
1: phage containing the peptide of SEQ ID NO: 32,
2: phage containing the peptide of SEQ ID NO: 33, and
3 and 4: control phages which do not contain the peptide of SEQ ID NO: 32 or 33

Selected phage clones are subjected to nucleotide sequencing, and amino acid sequences deduced from the analyzed nucleotide sequences have the amino acid sequences of SEQ ID NOs: 32 and 33, which are found to bind to c-MET (see FIG. 6). These results suggest that an antigen binding site of anti-HGF antibody H61 or H68 mimics a HGF binding site of c-MET and the peptides of SEQ ID NOs: 32 and 33 binding to anti-HGF antibody H61 or H68 mimic a c-MET binding site of HGF. Accordingly, the inventive peptides of SEQ ID NOs: 32 and 33 are capable of functioning as a neutralizable epitope of HGF.

Further, the present invention provides the polynucleotide encoding said neutralizable epitope. In particular, said neutralizable epitope has the nucleotide sequence of SEQ ID NO: 34 or 35.

Furthermore, the present invention provides a neutralizing antibody against HGF which is capable of neutralizing HGF by binding to the peptide of SEQ ID NO: 32 or 33 as a neutralizable epitope of HGF.

The neutralizing antibody of the present invention may be a chimeric antibody, a monoclonal antibody or a humanized antibody.

The chimeric antibody is an immunoglobulin molecule comprising human and non-human portions. Specifically, the antigen combining region (variable region) of a chimeric antibody is derived from a non-human source (e.g. mouse, rabbit, poultry) and the constant region of the chimeric antibody which confers the biological effector function to the immunoglobulin is derived from a human source. The chimeric antibody should have the antigen binding specificity of the non-human antibody molecule and the effector function conferred by the human antibody molecule.

In general, the procedures used to produce chimeric antibodies involve the following steps:

(a) identifying and cloning the correct gene segment encoding the antigen binding portion of the antibody molecule, which (known as $V_{DJ}$, variable, diversity and joining regions for heavy chains or $V_J$, variable, joining regions for light chains or simply as V for variable region) may be in either the cDNA or genomic form;

(b) cloning gene segments encoding the constant region or desired part thereof;

(c) ligating the variable region with the constant region so that the complete chimeric antibody is encoded in a form that can be transcribed and translated;

(d) ligating the construct into a vector containing a selectable marker and gene control regions such as promoters, enhancers and poly(A) addition signals;

(e) amplifying the vector and introducing it into eukaryotic cells (transfection), usually mammalian lymphocytes;

(f) selecting cells expressing the selectable marker;

(g) screening for cells expressing the desired chimeric antibody; and (h) testing the antibody for appropriate binding specificity and effector functions.

A monoclonal antibody refers to an antibody that is derived from a single clone, including any eukaryotic, prokaryotic, or phage clone. The monoclonal antibody may comprise, or consist of, two proteins, i.e., heavy and light chains. The monoclonal antibody can be prepared using one of a wide variety of techniques known in the art including the use of hybridoma, recombinant, and phage display technologies, or a combination thereof.

A humanized antibody refers to a molecule that has its CDRs (complementarily determining regions) derived from a non-human species immunoglobulin and the remainder of the antibody molecule derived mainly from a human immunoglobulin. The term "antibody" as used herein, unless indicated otherwise, is used broadly to refer to both an antibody molecule and an antibody-derived molecule. Such an antibody-derived molecule comprises at least one variable region (either a heavy chain or a light chain of variable region) and includes molecules such as Fab fragments, Fab' fragments, F(ab').sub.2 fragments, Fd fragments, Fab' fragments, Fd fragments, Fabc fragments, Sc antibodies (single chain antibodies), diabodies, individual antibody light chains, individual antibody heavy chains, chimeric fusions between antibody chains and other molecules.

In particular, the present invention provides a rabbit/human chimeric antibody as a neutralizing antibody against HGF. The inventive neutralizing antibody comprises $V_H$ region of SEQ ID NO: 27 and $V_L$ of SEQ ID NO: 28 or $V_H$ region of SEQ ID NO: 29 and $V_L$ of SEQ ID NO: 30.

Whether or not a neutralizing antibody exerts neutralizing activity may be examined by MDCK2 scattering assay (Cao et al., PNAS 98(13): 7443-7448, 2001). In case of treating 2 ng/ml of HGF (29 pM) to MDCK2 cells, the inventive neutralizing antibody shows the highest scattering inhibitory activity when the molar ratio of anti-HGF Fab to HGF becomes 50:1, and the molar ratio of anti-human Fab to HGF, ranging from 50:1 to 100:1 (see FIG. 9). These results show for the first time that blocking of only one epitope is sufficient for neutralizing HGF at least in vitro, different from the Cao report that it is necessary to neutralize at least three epitopes to inhibit MDCK2 cell scattering (Cao et al., supra). Further, shown in the present invention is the fact that the neutralizing antibody exerts its neutralizing activity only when the antibody binding to the neutralizable epitope is divalent or more, which suggests that the same neutralizable epitope may exist at two or more sites of HGF.

The binding affinity of anti-HGF Fab for HGF, inhibitory activity of clone 68 for binding HGF to c-Met, and inhibitory activity of soluble c-Met for binding HGF to c-Met may also be examined by EIA. The amount of clone 68 antibody binding to HGF immobilized on a sensor chip increases with the injection amount of clone 68 antibody (see FIG. 10), and the amount of HGF binding to c-Met decreases as the concentration of clone 68 antibody increases (see FIG. 11). Further, the amount of HGF binding to c-Met immobilized on the sensor chip decreases with increasing the concentration of soluble c-Met (see FIG. 12).

The above results demonstrate that the inventive neutralizing antibody acts as a single agent which is capable of neutralizing HGF.

Accordingly, the present invention further provides a pharmaceutical composition comprising an effective dose of the inventive neutralizing antibody and a pharmaceutically acceptable carrier for preventing and treating intractable diseases and cancers caused by the binding of HGF to a receptor thereof. Further, the present invention provides a method for preventing and treating intractable diseases and cancers by using the inventive neutralizable antibody. Preferably, the cancer includes, but are not limited to, various human cancers of liver, prostate, colon, breast, brain and skin, and the intractable diseases encompasses those caused by binding HGF to its receptor, c-Met, and include, not but limited to, malaria, Alzheimer's disease and so on.

The inventive pharmaceutical formulation may be prepared in accordance with any one of the conventional procedures. In preparing the formulation, the effective ingredient is preferably admixed or diluted with a carrier. Examples of suitable carriers, excipients, or diluents are lactose, dextrose, sucrose, sorbitol, mannitol, starches, gum acacia, alginates, gelatin, calcium phosphate, calcium silicate, cellulose, methylcellulose, microcrystalline cellulose, polyvinylpyrrolidone, water, methylhydroxybenzoates, propylhydroxybenzoates, talc, magnesium stearate and mineral oil. The formulation may additionally include fillers, anti agglutinating agents, lubricating agents, wetting agents, flavoring agents, emulsifiers, preservatives and the like. The composition of the invention may be formulated so as to provide a quick, sustained or delayed release of the active ingredient after it is administered to a patient, by employing any one of the procedures well known in the art.

The pharmaceutical formulation of the present invention can be administered by injection (e.g., intramuscular, intravenous, intraperitoneal, subcutaneous), or by other methods such as infusion that ensure its delivery to the bloodstream in an effective form. The pharmaceutical formulation may also be administered by intratumoral, peritumoral, intralesional or perilesional routes, to exert local as well as systemic therapeutic effects. Local or intravenous injection is preferred injection.

For treating a human patient, a typical daily dose of the inventive neutralizing antibody as an effective ingredient may range from about 0.1 to 100 mg/kg body weight, preferably 1 to 10 mg/kg body weight, and can be administered in a single dose or in divided doses. However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

EXAMPLE 1

HGF Immunization and Antibody Library Construction

Over a period of 4 to 5 months, 2 rabbits of the New Zealand White strain were immunized by 5 cutaneous injections of HGF (R&D systems, USA) dispersed in an emulsion of MPL (monophosphoryl lipid A; highly-refined non-toxic lipid A isolated from remutants of *S. minnesota*)+TDM (synthetic trehalose dicorynomycolate; an analogue of trehalose dimycolate from the cord factor of the tubercle bacillus)+CWS (cell wall skeleton; from deproteinized and delipidated cell walls of mycobacteria) adjuvant (Sigma) at 3-week intervals. Antisera from the immunized animals were analyzed for their binding to recombinant human HGF (R&D systems or Research Diagnostics, Inc.) by ELISA using horseradish peroxidase-conjugated anti-rabbit Fc goat polyclonal antibodies (Pierce). As a result, it was found that while antisera obtained before HGF immunization almost never bind to HGF, antisera obtained after 5 cutaneous injections specifically bound to HGF.

Seven days after the final boost, the spleen and bone marrow were extracted from the immunized animals and used for total RNA preparation with TRI reagent (Molecular Research Center, Cincinnati, USA) and lithium chloride precipitation. First-strand cDNA was synthesized using the SUPERSCRIPT Preamlification System with oligo(dT) priming (Life Technologies, Inc.).

Rabbit/human chimeric antibody library was constructed according to the method described by Rader et al (Rader C. et al., *J. Biol. Chem.* 275: 13668-13676, 2000).

EXAMPLE 2

Amplification of Rabbit-Derived Ab Variable Region and Human-Derived Ab Constant Region (2-1) Amplification of Rabbit-Derived Ab Variable Region In order to amplify variable regions of rabbit $V_L$ ($V_\kappa$, $V_\lambda$) and $V_H$, PCR was performed by using primer combinations described in Table 1.

TABLE 1

| Variable region | Forward primer | Reverse primer |
|---|---|---|
| $V_\kappa$ | SEQ ID NO: 1 | SEQ ID NO: 4 |
| | SEQ ID NO: 1 | SEQ ID NO: 5 |
| | SEQ ID NO: 1 | SEQ ID NO: 6 |
| | SEQ ID NO: 2 | SEQ ID NO: 4 |
| | SEQ ID NO: 2 | SEQ ID NO: 5 |
| | SEQ ID NO: 2 | SEQ ID NO: 6 |
| | SEQ ID NO: 3 | SEQ ID NO: 4 |
| | SEQ ID NO: 3 | SEQ ID NO: 5 |
| | SEQ ID NO: 3 | SEQ ID NO: 6 |
| $V_\lambda$ | SEQ ID NO: 7 | SEQ ID NO: 8 |
| $V_H$ | SEQ ID NO: 9 | SEQ ID NO: 13 |
| | SEQ ID NO: 10 | SEQ ID NO: 13 |
| | SEQ ID NO: 11 | SEQ ID NO: 13 |
| | SEQ ID NO: 12 | SEQ ID NO: 13 |

A PCR reaction solution was prepared by mixing 1 μl of template cDNA (about 0.5 μg) synthesized in Example 1, 60 pmol of each primer, 10 μl of 10× PCR buffer, 8 μl of 2.5 mM dNTP mixture and 0.5 μl of Taq polymerase and adjusted to a final volume of 100 μl. The PCR condition was 30 cycles of 15 sec at 94° C., 30 sec at 56° C. and 90 sec at 72° C. after initial denaturation of 10 min at 94° C., and final extension of 10 min at 72° C. The amplified DNA was subjected to agarose gel electrophoresis and purified from the gel by using Qiaex gel extraction kit (Qiagen).

(2-2) Amplification of Human-Derived Ab Constant Region

PCR was conducted to amplify $C_{78}$ region of human-derived Ab constant region as follows: A PCR reaction solution was prepared by mixing 20 ng of pComb3XTT vector (Barbas et al., *Proc. Natl. Acad. Sci. USA* 15:88(18), 7978-82, 1991), 60 pmol of each primer (SEQ ID NOs: 14 and 15), 10 μl of 10× PCR buffer, 8 μl of 2.5 mM dNTP mixture and 0.5 μl of Taq polymerase and adjusted to a final volume of 100 μl. The PCR condition was 20 cycles of 15 sec at 94° C., 30 sec at 56° C. and 90 sec at 72° C. after initial denaturation of 10 min at 94° C., and final extension of 10 min at 72° C.

Meanwhile, PCR was performed to amplify $C_{H1}$ region of human-derived Ab constant region as follows: A PCR reaction solution was prepared by mixing 20 ng of pComb3XTT vector (Barbas et al., supra), 60 pmol of each primer (SEQ ID NOs: 16 and 17), 10 μl of 10× PCR buffer, 8 μl of 2.5 mM dNTP mixture and 0.5 μl of Taq polymerase and adjusted to a final volume of 100 μl. The PCR condition was 20 cycles of 15 sec at 94° C., 30 sec at 56° C. and 90 sec at 72° C. after initial denaturation of 10 min at 94° C., and final extension of 10 min at 72° C.

The amplified DNAs were subjected to agarose gel electrophoresis and purified from the gel by using Qiaex gel extraction kit (Qiagen).

EXAMPLE 3

Amplification of Light and Heavy Chains of Chimeric Antibody (3-1) Amplification of Light Chain PCR was carried out to amplify the light chain as follows: A PCR reaction solution was prepared by mixing 100 ng each of $V_L$ ($V_\kappa$, $V_\lambda$) PCR product purified in Example (2-1) and $C_\kappa$ PCR product purified in Example (2-2), 60 pmol each of primers (SEQ ID NOs: 18 and 15), 10 μl of 10× PCR buffer, 8 μl of 2.5 mM dNTP mixture and 0.5 μl of Taq polymerase and adjusted to a final volume of 100 μl. The PCR condition was 20 cycles of 15 sec at 94° C., 30 sec at 56° C. and 120 sec at 72° C. after initial denaturation of 10 min at 94° C., and final extension of 10 min at 72° C.

The amplified DNA was subjected to agarose gel electrophoresis and purified from the gel by using Qiaex gel extraction kit (Qiagen).

(3-2) Amplification of Heavy Chain

Overlap extension PCR was conducted to amplify Fd region ($V_H$ and $C_{H1}$) of a heavy chain as follows: A PCR reaction solution was prepared by mixing 100 ng each of $V_H$ PCR product purified in Example (2-1) and $C_{H1}$ PCR product purified in Example (2-2), 60 pmol each of primers (SEQ ID NOs: 19 and 17), 10 μl of 10× PCR buffer, 8 μl of 2.5 mM dNTP mixture and 0.5 μl of Taq polymerase and adjusted to a final volume of 100 μl. The PCR condition was 20 cycles of 15 sec at 94° C., 30 sec at 56° C. and 120 sec at 72° C. after initial denaturation of 10 min at 94° C., and final extension of 10 min at 72° C.

The amplified DNA was subjected to agarose gel electrophoresis and purified from the gel by using Qiaex gel extraction kit (Qiagen).

EXAMPLE 4

Preparation of Chimeric Fab Library

PCR was carried out to amplify chimeric rabbit/human Fab gene as follows: A PCR reaction solution was prepared by mixing 100 ng each of chimeric light chain product purified in Example (3-1) and the chimeric heavy chain product purified in Example (3-2), 60 pmol each of primers (SEQ ID NOs: 18 and 20), 10 μl of 10× PCR buffer, 8 μl of 2.5 mM dNTP mixture and 0.75 μl of Taq polymerase and adjusted to a final volume of 100 μl. The PCR condition was 20 cycles of 15 sec at 94° C., 30 sec at 56° C. and 180 sec at 72° C. after initial denaturation of 10 min at 94° C., and final extension of 10 min at 72° C.

The amplified DNA was subjected to agarose gel electrophoresis and purified from the gel by using Qiaex gel extraction kit (Qiagen).

Figure 2:
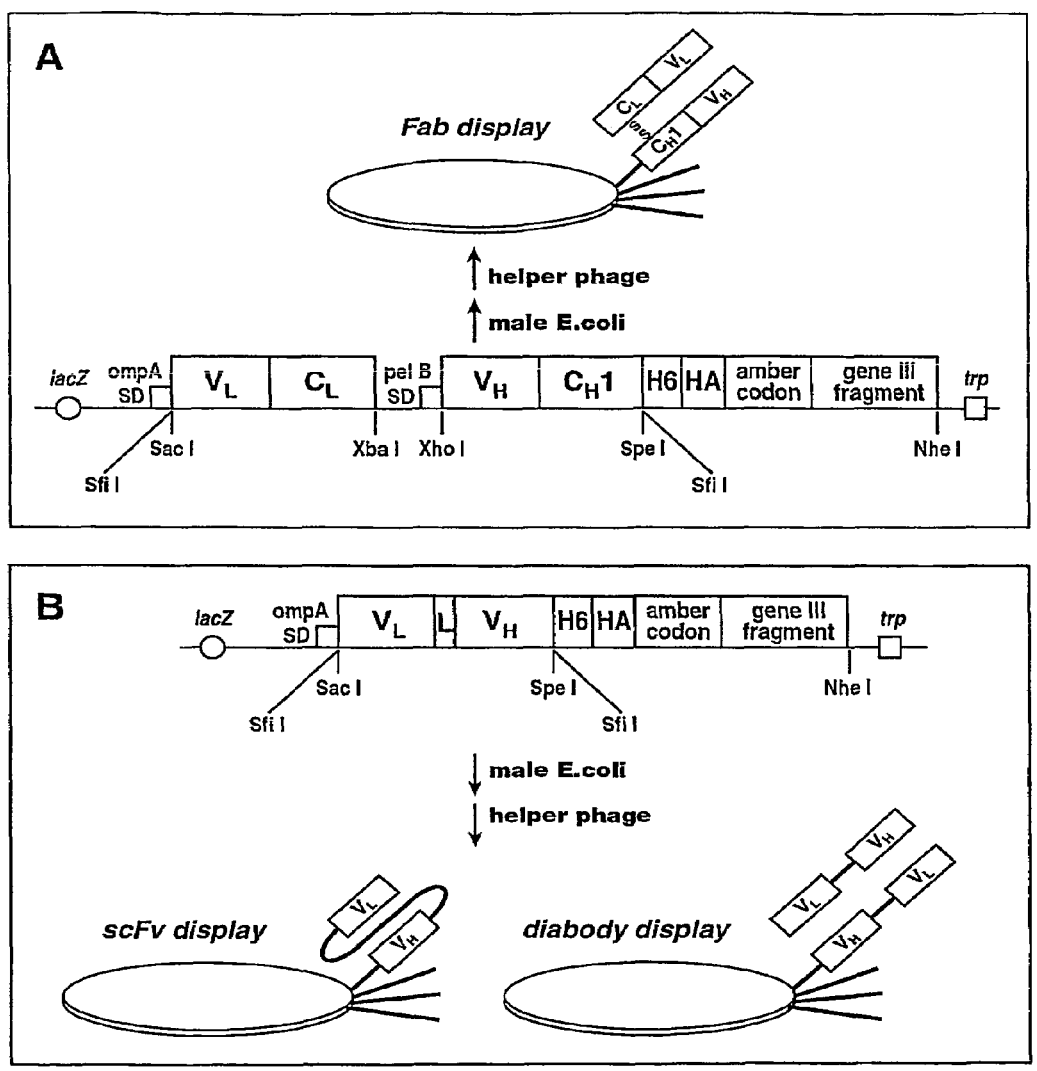
FIG. 2: the genetic map of phagemid vector pComb3X used for antibody library construction, A: the case of displaying Fab on the surface of phagemid, and B: the case of displaying scFv or diabody on the surface of phagemid

After the PCR products encoding rabbit $V_L$ and $V_H$ sequences were combined with the PCR products encoding human $C_\kappa$ and $C_{H1}$ sequences, final PCR fragments encoding a library of antibody fragments were subjected to SfiI digestion and cloned into phagemid vector pComb3X (the Scripps Research Institute, CA, USA) (FIG. 2). Phagemid DNA was transformed into *E. coli* ER2537 (NEB) by electrophoration. The introduced phage displayed Fab as a fusion protein fused on phage coat protein pIII and its DNA formed a phage particle (gene and polypeptide as one unit) in the phage DNA.

EXAMPLE 5

Selection of Phage Clone Containing Anti-HGF Fab

Figure 3:
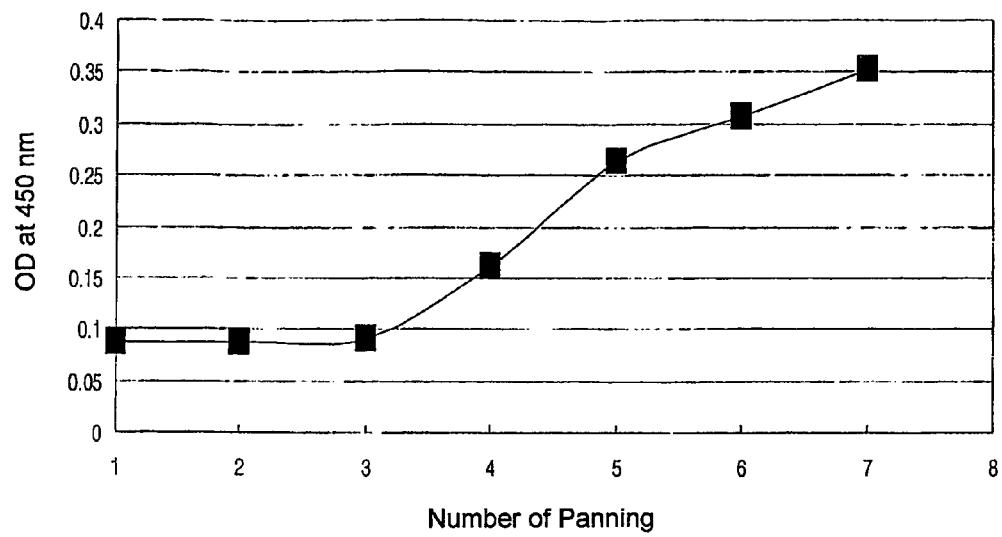
FIG. 3: enrichment of the phage pool displaying Fab specifically binding to HGF through the panning during the culture of HGF-binding clones.
Figure 7:
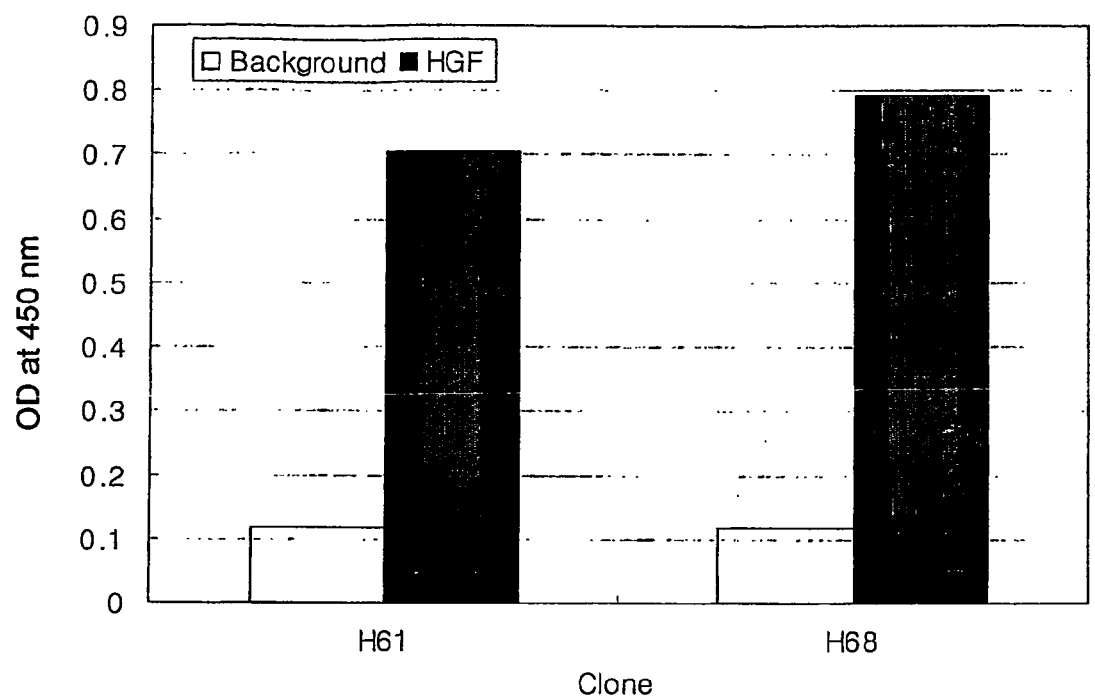
FIG. 7: the specific binding of clone 61 and 68 Fabs to HGF, respectively.

After a 96-well plate (Costar No. 3690) was coated with HGF dissolved in 25 μl of TBS solution at a concentration of 10 μl/ml per well, phages displaying Fab prepared in Example 4 were added to the well plate, the well plate was kept at room temperature for 2 hrs, and panned against immobilized HGF antigen at the well plate. The well plate was washed with 0.5% (v/v) Tween 20 in PBS and eluted with 0.1 M HCl-glycine (pH 2.2). The washing steps were increased from 5 times in the first round to 10 times in the second round and 15 times in the following rounds. Typically seven rounds of panning were conducted. As the panning proceeded, phage pools displaying anti-HGF Fab which specifically bind to HGF increased, which results in increasing absorbance showing the HGF binding to Fab in EIA using HRP-conjugated anti-M13 phage antibodies (Pharmacia) and HGF-coated ELISA plates (FIG. 3). After the last round of panning, the page clones containing anti-HGF Fab were selected by EIA using the HGF-coated ELISA plates and goat anti-human Fab polyclonal antibodies (Pierce), respectively. The selected clones were designated H61 (clone 61) and H68 (clone 68). H61 and H68 clones which gave strong signals above background (FIG. 7) were further analyzed by nucleotide sequencing.

EXAMPLE 6

Nucleotide Sequencing Analysis of Selected Phases

Nucleotide sequencing was carried out by the dye labeled primer sequencing method (Chung et al., *J. Cancer Res. Clin. Oncol.* 128: 641-649, 2002) using two sequencing primers of SEQ ID NOs: 21 and 22. As a result, it was found that H61 clone encodes the anti-HGF Fab consisting of $V_H$ region having the nucleotide sequence of SEQ ID NO: 23 and $V_L$ region having the nucleotide sequence of SEQ ID NO: 24; and H68 clone, the anti-HGF Fab consisting of $V_H$ region having the nucleotide sequence of SEQ ID NO: 25 and $V_L$ region having the nucleotide sequence of SEQ ID NO: 26.

The amino acid sequences of H61 and H68 clones were deduced from the analyzed nucleotide sequences, respectively. As a result, it was found that $V_H$ and $V_L$ regions of H61 clone had the amino acid sequences of SEQ ID NO: 27 and 28, respectively, while $V_H$ and $V_L$ regions of H68 clone had the amino acid sequences of SEQ ID NO: 29 and 30, respectively.

As a result of analyzing a framework region (FR) and complementarity determining region (CDR) in the amino acid sequences of H61 and H68 clones according to the method described by Harris (Harris et al., *Protein Science* 4(2): 306-10, 1995), H61 and H68 clones had the regional constituents described in Table 2.

TABLE 2

| Region | H61 clone $V_H$ | H61 clone $V_L$ | H61 clone $V_H$ | H61 clone $V_L$ |
| --- | --- | --- | --- | --- |
| FR1 | 1-30 | 1-23 | 1-30 | 1-23 |
| CDR1 | 31-35 | 24-34 | 31-35 | 24-34 |
| FR2 | 36-49 | 35-49 | 36-49 | 35-49 |
| CDR2 | 50-66 | 50-56 | 50-66 | 50-56 |
| FR3 | 67-98 | 57-88 | 67-98 | 57-88 |
| CDR3 | 99-105 | 89-97 | 99-105 | 89-97 |
| FR4 | 106-116 | 98-109 | 106-116 | 98-109 |

EXAMPLE 7

Anti-HGF Fab Expression and Purification for in vitro Assay

Phagemid DNAs of the selected clones in Example 5 were transformed into non-suppressor *E. coli* strain HB2151. Clones were grown to an A600 nm absorbance of 0.5 to 1.0 and induced the expression of anti-HGF Fab with IPTG (1 mM) for 20 to 24 hrs. Culture supernatants were concentrated by Labscale TFF system (Millipore). Concentrated anti-HGF Fab was purified by affinity chromatography using anti-HA tag mouse monoclonal antibody. Purified Fab fragments were analyzed by Coomassie staining and western blotting.

Figure 4:
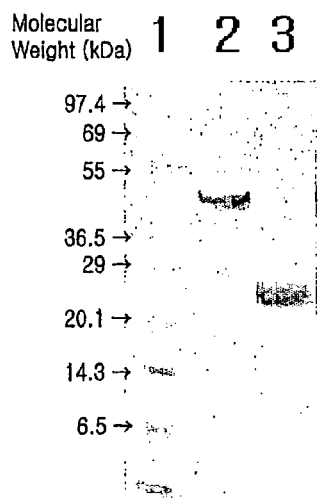
FIG. 4: the result of staining the purified Fab fragments with coomasie blue,
1: marker,
2: non-reduced clone 68 antibody (50,000 Da), and
3: reduced clone 68 antibody (25,000 Da)

First, the purified H68 antibody Fab (about 1-3 μg) was subjected to electrophoresis by loading on NuPAGE Novex 4-12% Bis-Tris Gel (Invitrogen). The loaded gel was soaked in a coomassie gel staining solution (Invitrogen), stirred for 30 min, transferred into a coomassie gel destaining solution, and stirred until developed protein bands were observed. FIG. 4 shows the result of coomassie staining. As shown in FIG. 4, in case of non-reduced H68 antibody (lane 2), most of Fab antibodies were detected at a position corresponding to a molecular weight of 50,000 Da; in case of reduced H68 antibody (lane 3), Fab antibody was separated into the respective Fd regions of light and heavy chains, and therefore, bands were detected at a position corresponding to 25,000 Da; and other bands except antibody bands were not detected. In view of facts that light and heavy chains of H68 antibody Fab are of the size of about 25,000 Da, respectively, and Fab formed by covalently linking between the light and heavy chains by a disulfide bond has the size of about 50,000 Da, the H68 antibody Fab was successively isolated and purified to a satisfiable purity. However, the weak band detected in lane 2 at a position corresponding to 25,000 Da is due to the presence of free Fd regions of Fab light and heavy chains that are not linked to each other.

Meanwhile, for western blotting, the purified anti-HGF Fab (about 1-3 μg) was subjected to electrophoresis by loading on NuPAGE® Novex 4-12% Bis-Tris Gel (Invitrogen) (polyacrylamide gel system for high performance gel electrophoresis). The Fab separated according to molecular weight was immobilized onto BioTrace Nitrocellulose membrane (PALL). The membrane was treated with 5% non-fat dry milk/TBS for 30 min to block. Horseradish peroxidase-conjugated anti-human goat Fab polyclonal antibody (Pierce) was diluted with 3% non-fat dry milk/TBS in a ratio of 1:1000 and reacted with the membrane for 1 hr with stirring. The membrane was washed with TBS for 30 min and wetted evenly with an equal volume mixture of Supersignal West Pico stable peroxide solution (Pierce) and Supersignal West Pico Luminol/Enhancer solution (Pierce). The membrane was exposed to X-ray film (Kodak) in a darkroom.

Figure 5:
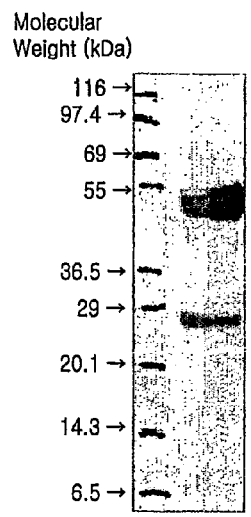
FIG. 5: the result of western blotting analysis to determine whether the purified Fan fragments are expressed.

FIG. 5 shows the result of western blotting analyzing the expression of purified Fab fragments, wherein the left lane is a size marker and other lanes are the purified Fabs. As shown in FIG. 5, a large quantity of Fab was detected at a position corresponding to 50,000 Da, and free Fd regions of light and heavy chains, at a position corresponding to 25,000 Da.

EXAMPLE 8

Analysis of Nucleotide Sequence and Features of HGF Neutralizable Epitope (8-1) Nucleotide Sequencing A 96-well plate (costar No. 3690) was coated with anti-HGF H61 Fab or anti-HGF H68 Fab dissolved in 25 μl of TBS solution at a concentration of 10 μg/ml per well. PHD peptide library (phage display of combinatorial peptide library) (new England Biolob.) was added to the well plate, and then, the well plate was kept for 2 hrs at room temperature. The well plate was washed with 0.5% (v/v) Tween 20 in PBS and eluted with 0.1 M HCl-glycine (pH 2.2). The washing steps were increased from 5 times in the first round to 10 times in the second round and 15 times in the subsequent rounds. Typically seven rounds of panning were carried out. After the last round of panning, the phage clones containing anti-HGF H61 Fab or anti-HGF H68 Fab were selected by EIA using anti-HGF H61 Fab or anti-HGF H68 Fab-coated ELISA plate and horseradish peroxidase-conjugated anti-M13 phage goat monoclonal antibody (Roche). The selected clones were subjected to nucleotide sequencing and the amino acid sequences were determined from the analyzed nucleotide sequences.

Nucleotide sequencing was performed according to the dye-labeled primer sequencing method (Chung et al., supra) using a sequencing primer of SEQ ID NO: 31. As a result, peptides encoding anti-HGF H61 and H68 Fabs deduced from the analyzed nucleotide sequences had the amino acid sequences of SEQ ID NOs: 32 and 33, respectively.

Then, a 96-well plate (costar No. 3690) was coated with c-Met dissolved in 25 μl of TBS solution at a concentration of 10 μg/ml per well, and clones containing the peptides of SEQ ID NOs: 32 and 33 were each added thereto. The well plate was washed with 0.5% (v/v) Tween 20 in PBS, and horseradish peroxidase-conjugated anti-M13 phage goat monoclonal antibody (Roche) was added thereto.

As shown in FIG. 6, while the phages containing the respective peptides (1 and 2) of SEQ ID NO: 32 and 33 bound to c-Met, two control phages (3 and 4) without said peptides did not. These results suggest that since an antigen binding site of anti-HGF antibody H68 mimics a HGF binding site of c-Met and the peptides of SEQ ID NOs: 32 and 33 binding to clone 68 mimic c-Met binding site of HGF, the peptides of SEQ ID NOs: 32 and 33 can function as a neutralizable epitope of HGF.

(8-2) Characterization

In order to characterize the antigen binding site of anti-HGF antibody, western blotting was carried out as follows. 1 to 3 μg of HGF was subjected to electrophoresis by loading on NUPAGE Novex 4-12% Bis-Tris Gel (Invitrogen). At this time, some were loaded after treating with a reducing agent, and others were loaded without such reducing agent treatment. Proteins separated according to molecular weight were immobilized onto BioTrace Nitrocellulose membrane (PALL). The membrane was each treated with 5% non-fat dry milk/TBS for 30 min to block. Anti-HGF H61 and H68 Fabs were added to the membrane, and the membrane was stirred for 1 hr. Horseradish peroxidase-conjugated anti-human goat Fab polyclonal antibody (Pierce) was diluted with 3% non-fat dry milk/TBS in a ratio of 1:1000 and reacted with the membrane for 1 hr with stirring. The membrane was washed with TBS for 30 min and wetted evenly with an equal volume mixture of Supersignal West Pico stable peroxide solution (Pierce) and Supersignal West Pico Luminol/Enhancer solution (Pierce) for 30 min. The membrane was exposed to X-ray film (Kodak) in a darkroom.

Figure 8:
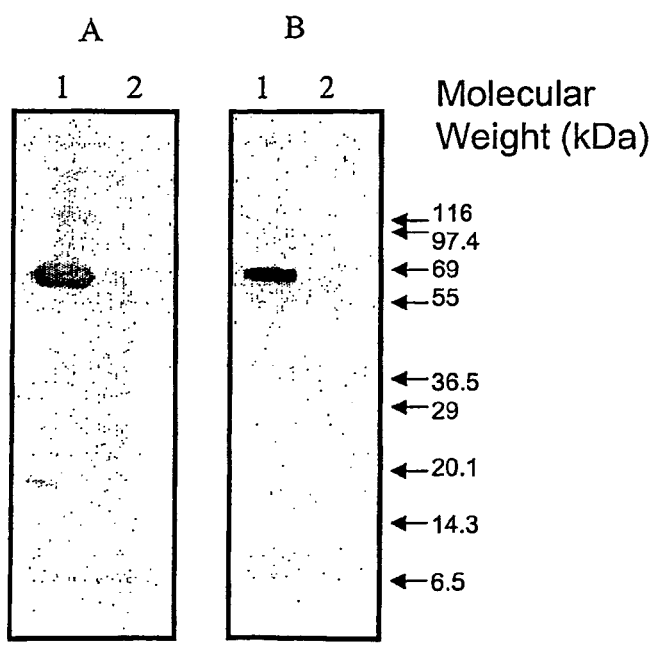
FIG. 8: conformation dependency of the inventive neutralizable epitope defined by clones 61 and 68, respectively,
A: clone 61,
B: clone68,
Lane 1: non-reduced HGF, and
Lane 2: reduced HGF

FIG. 8 shows conformation dependency of the neutralizable epitopes defined by H61 and H68, wherein an arrow indicates a size marker; A, clone 61; B, clone 68; lane 1, a non-reduced HGF; and lane 2, a reduced HGF. As a result, clones 61 and 68 were found to bind to the non-reduced HGF, but not to the reduced HGF. These results suggest that the tertiary structure of the antigenic determinants, e.g., epitopes, serving as binding sites of clones 61 and 68, are crucial for antigen-antibody response and the inventive neutralizable epitopes has a non-linear structure.

EXAMPLE 9

MDCK Scattering Assay

Figures 9A, 9B:
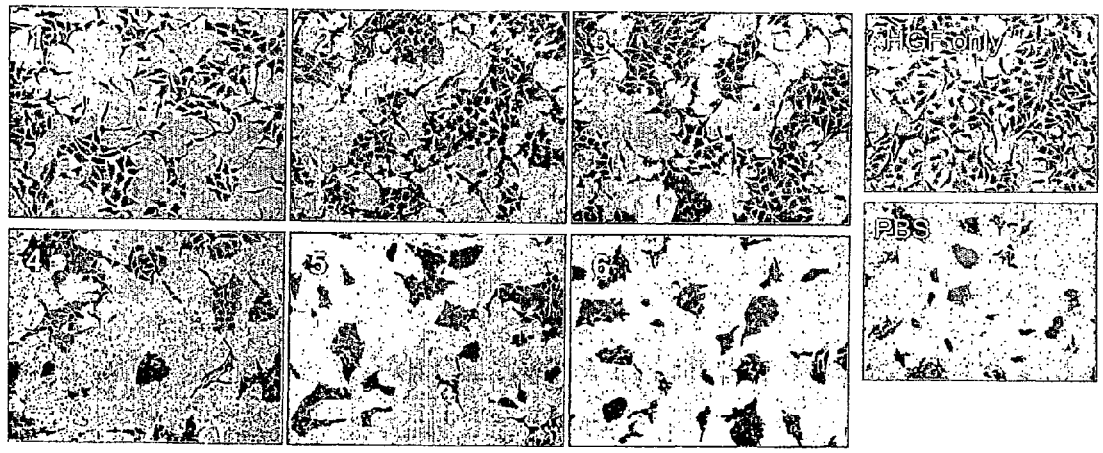
FIG. 9a: the criteria showing the cell scattering level ranging from Grades 1 to 6.
FIG. 9b: the result of scattering assay showing that the scattering levels of anti-HGF Fab and anti-human Fab antibodies change with the concentrations of HGF added.

MDCK cells (Nadine Darby canine kidney cells; ATCC CCL 34) were cultured in a DMEM medium supplemented with 5% FCS at 37° C. in a humid chamber under 95% air and 5% $CO_2$. Cells were distributed on a 96-well plate at a concentration of $2 \times 10^3$ cells/well and exposed to 2 ng/ml (29 pM) of HGF in a fresh medium overnight. Then, anti-HGF Fab and anti-human Fab antibodies were added to the well plate at different concentrations. The scattering effect was monitored by light microscopy, and the result is shown in FIG. 9. FIG. 9*a* shows the criteria indicating the cell scattering level ranging from Grades 1 to 6, wherein Grade 6 means 100% inhibition of scattering effect by HGF; Grade 5, inhibition ranging from 90 to 100% of scattering effect by HGF; Grade 4, inhibition ranging from 60 to 90% of scattering effect by HGF; Grade 3, inhibition ranging from 30 to 60% of scattering effect by HGF; Grade 2, inhibition ranging from 10 to 30% scattering effect by HGF; and Grade 1, 10% and less inhibition of scattering effect by HGF. FIG. 9*b* shows that the scattering levels of anti-HGF Fab and anti-human Fab antibodies may differ according to the concentrations of HGF added.

As a result, it was found that the most effective scattering effect was expected when the molar ratio of anti-HGF Fab to HGF was 50:1 and the molar ratio of anti-human Fab antibody to HGF was ranging from 50:1 to 100:1.

EXAMPLE 10

BIAcore Assay (10-1) Affinity Analysis of Anti-HGF Fab for HGF

The binding affinity of anti-HGF Fab for HGF was determined by SPR (surface plasmon resonance) using the BIAcore 3000 (BIAcore AB, Uppsala, Sweden).

Figure 10:
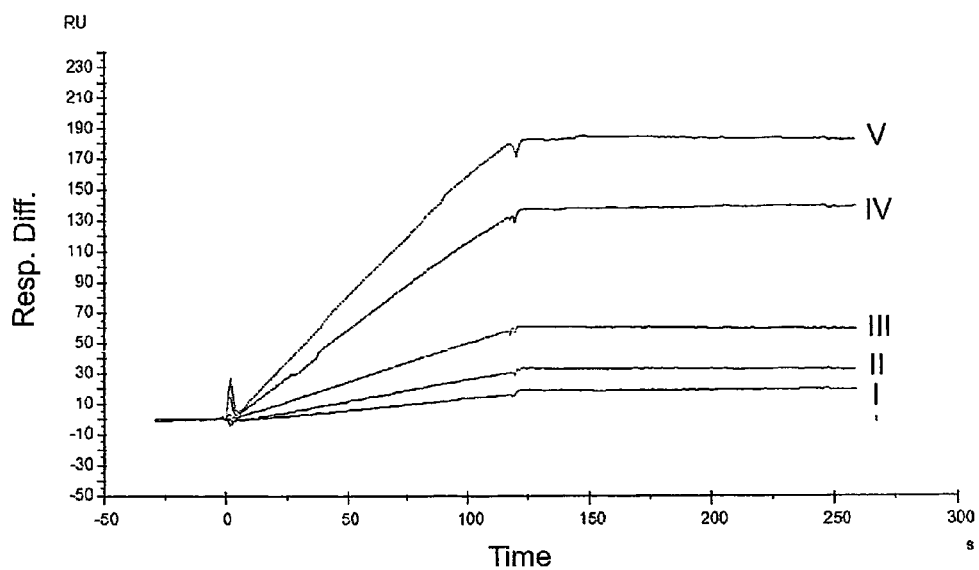
FIG. 10: the amount of clone 68 antibody bound to HGF immobilized on CM5 sensor chip increases with the injected amount of clone 68 antibody,
I: injection of non-specific Fab,
II: injection of 50 nM clone 68 antibody,
III: injection of 100 nM clone 68 antibody,
IV: injection of 200 nM clone 68 antibody,
V: injection of 400 nM clone 68 antibody, and
VI: injection of 600 nM clone 68 antibody

Approximately, 1069 resonance units (RU) of HGF were coupled to CM5 sensor chip (BIAcore AB) through an amine coupling method. Binding interaction was allowed to proceed in PBS buffer containing 0.005% surfactant P20 at a flow rate of 30 μl/min at 25° C. The surface was regenerated with 1 M NaCl/50 mM NaOH. The kinetic rate constants ($k_{on}$ and $k_{off}$) as well as the equilibrium dissociation constant ($K_d$) were determined. FIG. 10 shows the binding affinity of anti-HGF H68 Fab for HGF. As a result, it was found that the amount of anti-HGF H68 Fab bound to HGF immobilized on the sensor chip increases with the concentration of anti-HGF H68 Fab.

(10-2) Analysis of HGF Binding Inhibitory Activity of Clone 68 Antibody Against HGF To ascertain the fact that anti-HGF H68 Fab can inhibit the binding of HGF to c-Met in real time, c-Met was coupled to CM5 sensor chip through an amine coupling method. Thereafter, HGF alone was injected at a concentration of 50 nM, and premixed with anti-HGF H68 Fab of 5 different concentrations (50 nM, 250 nM, 500 nM, 1 μM and 1.5 μM) and soluble c-Met of 5 different concentrations (50 nM, 100 nM, 200 nM, 400 nM, 600 nM), respectively. Binding interaction was allowed to proceed in PBS buffer containing 0.005% surfactant P20 at a flow rate of 30 μl/min at 25° C. The surface was regenerated with 1 M NaCl/50 mM NaOH.

Figure 11:
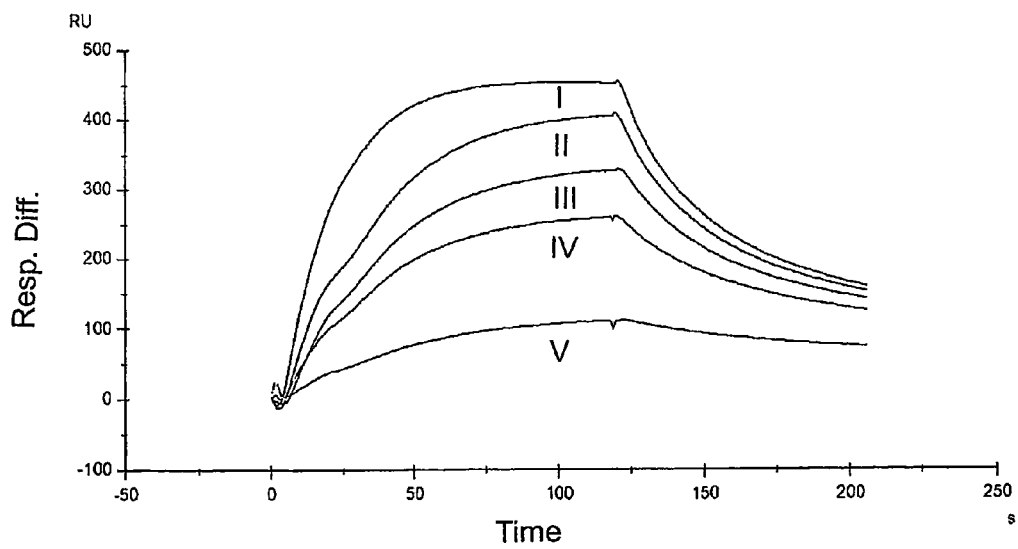
FIG. 11: clone 68 antibody inhibits the binding of HGF to c-Met,
I: injection of 50 nM HGF,
II: injection of 50 nM HGF mixed with 50 nM clone 68 antibody,
III: injection of 50 nM HGF mixed with 250 nM clone 68 antibody,
IV: injection of 50 nM HGF mixed with 500 nM clone 68 antibody,
V: injection of 50 nM HGF mixed with 1 µM clone 68 antibody, and
VI: injection of 50 nM HGF mixed with 1.5 µM clone 68 antibody

FIG. 11 shows that anti-HGF H68 Fab inhibits the binding of HGF to c-Met. As a result, in case of 50 nM HGF injection, HGF was found to bind to c-Met at 455.5 RU (I), while in case of 50 nM HGF injection with anti-HGF H68 Fab at 5 different concentrations of 50 nM (II), 250 nM (E), 500 nM (IV), 1 μM (V) and 1.5 μM (VI), HGF bound to c-Met at 406.5, 328, 260, 111.1 and 71 RU, respectively. These results suggest that the binding of HGF to c-Met becomes reduced as the concentrations of anti-HGF H68 Fab increases. There was no binding of HGF in case when anti-HGF H68 Fab alone was injected.

(10-3) Analysis of HGF Binding Inhibitory Activity of Soluble c-Met Against c-Met Whether the binding of HGF to c-Met is inhibited by soluble c-Met was examined as follows. 2979 RU of c-Met was immobilized on CM5 sensor chip through an anime coupling method. Binding interaction was allowed to proceed in PBS buffer containing 0.005% surfactant P20 at a flow rate of 30 μl/min at 25° C. The surface was regenerated with 1 M NaCl/50 mM NaOH.

Figure 12:
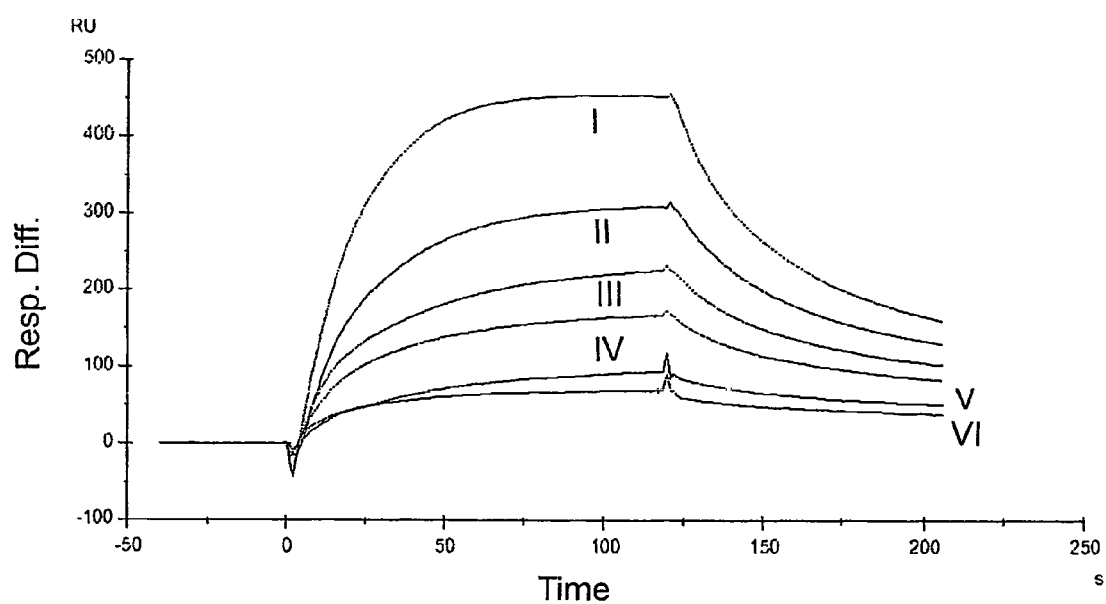
FIG. 12: soluble c-Met inhibits the binding of HGF to c-Met.
I: injection of 50 nM HGF,
II: injection of 50 nM HGF mixed with 50 nM soluble c-Met,
III: injection of 50 nM HGF mixed with 100 nM soluble c-Met,
IV: injection of 50 nM HGF mixed with 200 nM soluble c-Met,
V: injection of 50 nM HGF mixed with 400 nM soluble c-Met, and
VI: injection of 50 nM HGF mixed with 600 nM soluble c-Met

FIG. 12 shows that soluble c-Met inhibits the binding of HGF to c-Met. As shown in FIG. 12, in case of 50 nM HGF injection, HGF was found to bind to c-Met at 455.5 RU (I); while in case of 50 nM HGF injection with soluble c-Met at 5 different concentrations of 50 nM (II), 100 nM (III), 200 nM (IV), 400 nM (V) and 600 nM (VI), HGF bound to c-Met at 310.3, 225.7, 167.4, 93.7 and 70.9 RU, respectively. These results suggest that the amount of HGF binding to c-Met immobilized on the sensor chip gradually decreases with increasing concentration of soluble c-Met increases.

While the embodiments of the subject invention have been described and illustrated, it is obvious that various changes and modifications can be made therein without departing from the spirit of the present invention which should be limited only by the scope of the appended claims.

What is claimed is:

1. An isolated neutralizing antibody wherein said antibody comprises a VH region comprising the amino acid sequence of SEQ ID NO: 27 and a VL region comprising the amino acid sequence of SEQ ID NO: 28, and wherein said antibody inhibits the binding of hepatocyte growth factor (HGF) to cMet.

2. An isolated neutralizing antibody wherein said antibody comprises a VH region comprising the amino acid sequence of SEQ ID NO: 29 and a VL region comprising the amino acid sequence of SEQ ID NO: 30, and wherein said antibody inhibits the binding of hepatocyte growth factor (HGF) to cMet.

3. The isolated neutralizing antibody of claim 1, which is selected from the group consisting of a chimeric antibody, a monoclonal antibody and a humanized antibody.

4. The isolated neutralizing antibody of claim 2, which is selected from the group consisting of a chimeric antibody, a monoclonal antibody and a humanized antibody.

5. The isolated neutralizing antibody of claim 1, which is an Fab.

6. The isolated neutralizing antibody of claim 2, which is an Fab.

* * * * *